(12) United States Patent
Pagliarini (10) Patent No.: US 10,287,152 B2
(45) Date of Patent: May 14, 2019

(54) APPARATUS AND METHOD FOR FILLING CONTAINERS (71) Applicant: GEA PROCOMAC S.P.A., Sala Baganza (Parma) (IT)

(72) Inventor: Paolo Pagliarini, Parma (IT)

(73) Assignee: GEA PROCOMAC S.P.A., Sala Baganza (IT)

( * ) Notice: Subject to any disclaimer, the term of this patent is extended or adjusted under 35 U.S.C. 154(b) by 34 days.

(21) Appl. No.: 15/520,366

(22) PCT Filed: Dec. 16, 2015

(86) PCT No.: PCT/IB2015/059689
§ 371 (c)(1),
(2) Date: Apr. 19, 2017

(87) PCT Pub. No.: WO2016/108125
PCT Pub. Date: Jul. 7, 2016

(65) Prior Publication Data
US 2017/0327365 A1 Nov. 16, 2017

(30) Foreign Application Priority Data

Dec. 30, 2014 (IT) .............................. PR2014A0112

(51) Int. Cl.
*B67C 3/22* (2006.01)
*B67C 7/00* (2006.01)
(Continued)

(52) U.S. Cl.
CPC .............. *B67C 7/0086* (2013.01); *A61L 2/14* (2013.01); *A61L 2/26* (2013.01); *B67C 3/26* (2013.01);
(Continued)

(58) Field of Classification Search
CPC ..... B67C 7/0086; B67C 7/004; B67C 7/0073; B67C 3/28; B67C 3/26; B67C 2003/228;
(Continued)

(56) References Cited

U.S. PATENT DOCUMENTS 5,819,817 A 10/1998 Van Nest
6,565,791 B1 * 5/2003 Laurent .................... A61L 2/14
264/129
(Continued)

FOREIGN PATENT DOCUMENTS

CN 1626434 6/2005
CN 201165466 12/2008
(Continued)

Primary Examiner — Nicolas A Arnett
(74) Attorney, Agent, or Firm — Pearne & Gordon LLP (57) ABSTRACT A method for filling a container (2) with a filling product, comprising the steps of: positioning the container (2) in a filling station (1) so that its mouth (2b) is below the filling valve (9); separating a treatment volume (40) of the neck (2a) comprised between the filling valve (9) and at least one part of the neck (2a) of the container (2) from an external environment (6) containing the body (2d) of the container (2); dispensing plasma into the treatment volume (40) so that it flows over the neck (2a) of the container (2); enabling the filling valve (9) to dispense the filling product into the container (2).

13 Claims, 9 Drawing Sheets (51) Int. Cl.
*A61L 2/14* (2006.01)
*A61L 2/26* (2006.01)
*B67C 3/26* (2006.01)
*B67C 3/28* (2006.01)

(52) U.S. Cl.
CPC ............... *B67C 3/28* (2013.01); *B67C 7/004* (2013.01); *B67C 7/0073* (2013.01); *A61L 2202/23* (2013.01); *B67B 2201/10* (2013.01); *B67C 2003/228* (2013.01); *B67C 2003/2688* (2013.01); *B67C 2003/2697* (2013.01)

(58) Field of Classification Search
CPC ..... B67C 2003/2688; B67C 2003/2697; A61L 2/26; A61L 2/14; A61L 2202/23; B67B 2201/10
See application file for complete search history.

(56) References Cited

U.S. PATENT DOCUMENTS

| | | | |
|---|---|---|---|
| 7,121,062 B2* | 10/2006 | Till | B67C 7/0086 53/167 |
| 7,165,582 B2* | 1/2007 | Till | B67C 7/0086 141/144 |
| 7,311,125 B2 | 12/2007 | Krulitsch | |
| 7,810,527 B2* | 10/2010 | Mouchelet | C23C 16/511 141/165 |
| 8,197,245 B2 | 6/2012 | Dordoni | |
| 8,268,257 B2* | 9/2012 | Frost | A61L 2/14 422/1 |
| 8,435,024 B2 | 5/2013 | Dordoni | |
| 8,482,206 B2 | 7/2013 | Pouvesle et al. | |
| 8,844,585 B2* | 9/2014 | Laumer | B67C 3/001 141/105 |
| 9,056,146 B2* | 6/2015 | Till | A61L 2/087 |
| 9,144,932 B2* | 9/2015 | Pagliarini | B29C 49/12 |
| 9,156,669 B2 | 10/2015 | Conforti et al. | |
| 9,186,856 B2 | 11/2015 | Pagliarini et al. | |
| 9,409,722 B2 | 8/2016 | Bruch et al. | |
| 2005/0092390 A1 | 5/2005 | Krulitsch | |
| 2005/0126118 A1* | 6/2005 | Till | B67C 7/0086 53/167 |
| 2008/0032059 A1* | 2/2008 | Zimmerer | A61L 2/14 427/458 |
| 2010/0272844 A1 | 10/2010 | Dordoni | |
| 2011/0018444 A1 | 1/2011 | Pouvesle et al. | |
| 2012/0018030 A1* | 1/2012 | Laumer | B67C 3/001 141/1 |
| 2012/0164258 A1 | 6/2012 | Dordoni | |
| 2012/0187073 A1 | 7/2012 | Conforti et al. | |
| 2013/0160405 A1* | 6/2013 | Preckel | B41J 3/4073 53/452 |
| 2014/0103584 A1 | 4/2014 | Pagliarini et al. | |
| 2015/0232283 A1 | 8/2015 | Bruch et al. | |
| 2017/0128604 A1* | 5/2017 | Shimizu | B01F 5/04 |
| 2017/0312977 A1* | 11/2017 | Pagliarini | B29C 49/06 |
| 2017/0326778 A1* | 11/2017 | Pagliarini | B29C 49/46 |
| 2017/0341287 A1* | 11/2017 | Pagliarini | B29C 49/061 |
| 2017/0362070 A1* | 12/2017 | Pagliarini | B67B 3/20 |

FOREIGN PATENT DOCUMENTS

| | | |
|---|---|---|
| CN | 102574670 B | 7/2012 |
| CN | 103112814 A | 5/2013 |
| DE | 1532584 A1 | 2/1970 |
| DE | 4219082 A1 | 12/1993 |
| DE | 19909826 A1 | 9/2000 |
| EP | 0780338 A1 | 6/1997 |
| EP | 1357081 A1 | 10/2003 |
| EP | 1520833 | 4/2005 |
| EP | 2246176 A1 | 11/2010 |
| EP | 2279850 A1 | 2/2011 |
| EP | 2340157 A1 | 7/2011 |
| EP | 2643142 A1 | 10/2013 |
| WO | 03011718 A2 | 2/2003 |
| WO | 2009050240 A1 | 4/2009 |
| WO | 2010149233 | 12/2010 |
| WO | 2014026732 A1 | 2/2014 |

* cited by examiner

APPARATUS AND METHOD FOR FILLING CONTAINERS

TECHNICAL FIELD

The present invention relates to an apparatus and a method for filling containers.

The reference sector is the bottling of so-called "sensitive" food products, i.e. products that are particularly sensitive to bacteriological contamination and oxidation, such as, for example, isotonic drinks, juices, nectars, soft drinks, tea, milk-based drinks, coffee-based drinks, etc., for which the prevention of possible microbiological contamination throughout all packaging stages is of fundamental importance.

BACKGROUND ART

Packaging lines using aseptic technology are already known, wherein the various operations take place in a controlled contamination environment, so that the bottled products can be stored for a prolonged period of time and have chemical/physical and organoleptic stability even at room temperature.

In the first installations containers were produced in non-aseptic apparatuses and subsequently the moulded containers were transferred into a cleanroom housing at least the filling machine and the capping machine.

Aside from differences in design, a "conventional" aseptic bottling line envisages:
- moulding the container starting with a parison made of a thermoplastic material;
- chemical sterilisation of the moulded container;
- rinsing, filling and capping of the filled container, to be performed within a cleanroom.

The cleanroom is a controlled contamination room which contains all the filling apparatus, including both the process zones in which the containers are effectively filled/capped, and the auxiliary zones in which the movement means of the filling machine/capping machine operates.

The main disadvantage of the cleanroom is therefore represented by its substantial volume, therefore lengthy and expensive sterilisation procedures are required. There is also considerable wastage of operating fluids, for example sanitisation liquids and sterile air, and wear phenomena, for example, of the filters needed to purify the air adapted to generate overpressure within the cleanroom so as to prevent the entry of contaminants from the external environment.

A further disadvantage of the use of a cleanroom regards the difficulty in performing format change, maintenance or machine part adjustment operations, due to the risk of contamination that such operations imply. Access to the cleanroom by an operator is therefore also particularly critical.

The evolution of aseptic technology has gone in the direction of reducing the volumes to be kept sterile.

A modern concept of an aseptic bottling line therefore envisages:
- sterilisation of the parison using chemical agents or radiation sterilisation;
- "aseptic" moulding of the container starting from the sterilized parison;
- filling and capping of the filled container, to be carried out in a sterile environment.

In this regard, the Applicant has developed a moulding apparatus for moulding under aseptic conditions, in which the moulding rotary carousel is protected by an isolator suitable for defining a controlled-contamination environment, and the movement means for moving the carousel and moulds is located outside of said isolator (see European patent EP2246176).

The preliminary sterilisation stage involves all devices that come into contact with the parison subjected to moulding by stretch-blowing, including for example the gripping members, the stretching rod and the blown air circuit. The Applicant has thus developed ad hoc solutions for the stretching rod (see European Patent no. EP2340157) and for the blown air circuit (European patent application no. EP 26443142).

In this way, the Applicant succeeded in developing a completely aseptic blowing machine and a bottling line wherein the process zone of each operating unit (e.g. filling machine and capping machine) is protected by a dedicated microbiological isolator, from which the movement and handling means of parisons/containers is excluded (see European patent EP2279850).

The main drawback of this solution clearly lies in the substantial structural complexity, the still considerable dimensions of the sterile zones (even if they are restricted and shaped around the operating units) and the difficulty to maintain sterile conditions within the isolators.

Furthermore, not all the manual procedures required during operation (e.g. removal of obstacles) can be performed with the use of handling gloves: in some cases, it may still be necessary to open the isolator access door, resulting in the loss of sterile conditions. Upon completion of the procedure, a sterile environment must be restored, resulting in an evident loss of time due to downtime of the line.

Still from this point of view, the format change operations are also long and not very practical.

Proceeding with the reduction of the volumes to be sterilised and the time necessary for performing the sterilisation procedures we find the solution described in document EP1357081, in relation to a filling machine in which the isolator has a toroidal extension conformed to cover the zones around the neck of the containers.

This configuration is a response to the brilliant intuition only to sterilise the surfaces of containers intended to come into contact with the filling product, i.e. the internal surfaces of containers or those near the opening, but excluding the external surfaces of the body of the containers.

However, this solution, known in the sector as a "neck-ring isolator" requires the provision of a further confinement of the body-zones of containers in order to prevent dispersions of the sterilising agents into the environment external to the toroidal isolator, with consequent risks to the health of the operators.

Therefore, the neck-ring isolator consists of a single volume in which the necks of containers transit which, however, also contains auxiliary members and elements, such as parts of transfer stars.

Therefore, even moving over to "neck-ring isolator" architecture, the problems of maintaining and/or restoring sterility remain.

DISCLOSURE OF THE INVENTION

In this context, the technical task underpinning the present invention is to provide an apparatus and method for filling containers which obviates the drawbacks of the prior art as cited above.

In particular, an object of the present invention is to provide an apparatus for filling containers wherein the volumes to be sterilised and the time needed for performing the sterilisation operations are further reduced with respect to the known solutions.

A further object of the present invention is to provide a method for filling containers that is quicker and more practical than the known methods, wherein the downtime due to restoring sterility along the line is further reduced.

The defined technical task and the specified objects are substantially reached by an apparatus for filling containers (2) with a filling product, comprising:
- a rotating carousel having a plurality of filling stations in each of which a filling valve is arranged below which the corresponding container can be positioned with its mouth facing said filling valve;
- means for separating a treatment volume of the individual neck of each container from an external environment containing the body of the container, the treatment volume being comprised between the corresponding filling valve and at least one part of the neck of the container;
- dispensing means for dispensing a fluid into the treatment volume of each neck so that it flows over the neck of the corresponding container in order to prevent the entry of contaminants into the treatment volume.

In the preferred embodiment, the means for separating the treatment volume from the external environment comprise, for each filling station, a tubular element external and concentric to the corresponding filling valve. Such tubular element can be moved linearly between at least one disengagement configuration and at least one engagement configuration of the mouth of the container placed below the filling valve.

In particular, the external environment is single and distinct from the individual treatment volumes of the filing stations. The treatment volumes are in fluid communication with the external environment.

Preferably, each filling valve is associated with a sanitisation device of the dummy bottle type which can be configured in at least one rest position wherein it prevents interference with the filling valve and in one active position wherein the dummy bottle is arranged below the filling valve closing the treatment volume so as to prevent fluid communication with the external environment.

Preferably, each treatment volume does not contain the bague of the corresponding container.

Preferably, the fluid dispensing means comprises:
- a plasma generator;
- a transport circuit for transporting the plasma from the plasma generator to the treatment volume.

In particular, the transport circuit in turn comprises conduits afforded in the filling valve laterally to a dispensing conduit for dispensing the filling product.

Preferably, the plasma generator is configured to generate balls of plasma immersed in a gas current.

Alternatively, the fluid dispensing means comprises a source of sterile air or a source of sterilising gas.

Preferably, the filling apparatus comprises:
- a first transfer star positioned upstream of the rotating carousel to transfer to the latter the containers to be filled;
- a second transfer star positioned downstream of the rotating carousel to receive the filled containers from the latter.

In particular, the first transfer star and the second transfer star have a plurality of picking stations for the containers, in each of which a concave shell is arranged. Preferably, the concave shell is configured to be applied onto the mouth of the corresponding container so as to be wrapped at least partially around its neck in order to delimit a treatment volume of the neck within which a flow of fluid is maintained that flows over the neck to prevent the entry of contaminants into the treatment volume.

Preferably, the first transfer star comprises:
- a first tunnel having an arched extension that follows the circumferential development of the first transfer star at least for a section that ends in proximity to the rotating carousel;
- first dispensing means of a cleaning fluid into the first tunnel.

In particular, the first tunnel towers over some of the concave shells of the first transfer star so that the cleaning fluid flows over its external surfaces. Preferably, the second transfer star comprises:
- a second tunnel having an arched extension that follows the circumferential development of the second transfer star at least for a section that starts in proximity to the rotating carousel;
- second dispensing means of a cleaning fluid into the second tunnel.

In particular, the second tunnel towers over some of the concave shells of the second transfer star so that the cleaning fluid flows over its external surfaces.

Preferably, the first and second cleaning fluid dispensing means consists of a plasma generator configured to generate balls of plasma immersed in a gas current.

Preferably, the filling apparatus comprises a shielding body arranged on the rotating carousel, which has a circumferential extension along a dead angle of the rotating carousel in which containers do not transit. Such a shielding body can be moved between a rest position wherein it avoids interfering with the filling valves that sweep through the dead angle and an active position wherein the shielding body is arranged below the filing valves that sweep through the dead angle to limit inverse air flows from the external environment towards the filling valves.

Preferably, the shielding body has an arched plate-like portion which is substantially orthogonal to the rotation axis of said rotating carousel.

The defined technical task and the specified objects are substantially reached by an apparatus for filling a container with a filling product, comprising the steps of:
- positioning the container in a filling station so that its mouth is below the filling valve;
- separating a treatment volume of the neck comprised between the filling valve and at least one part of the neck of the container by an external environment containing the body of the container;
- dispensing a flow of fluid into the treatment volume so as to flow over the neck of the container in order to prevent the entry of contaminants into the treatment volume;
- enabling the filling valve to dispense the filling product into the container.

Preferably, the step of separating the treatment volume from the external environment comprises a step of moving a tubular element, being external and concentric to the filling valve, towards the mouth of the container.

Preferably, the step of moving the tubular element towards the mouth of the container is interrupted before reaching the bague of the container.

BRIEF DESCRIPTION OF DRAWINGS

Further characteristics and advantages of the present invention will more fully emerge from the non-limiting description of a preferred but not exclusive embodiment of an apparatus and method for filling containers, as illustrated in the accompanying drawings, in which.

DETAILED DESCRIPTION OF PREFERRED EMBODIMENTS OF THE INVENTION

With reference to the figures, 10 indicates an apparatus for filling containers 2 with a filling product, for example with a drink.

The filling apparatus 10 comprises a rotating carousel 10a with a plurality of filling stations 1 in each of which a filling valve 9 is arranged below which the corresponding container 2 can be positioned with its mouth 2b facing towards the filling valve 9.

Originally, the filling apparatus 10 comprises means for separating 30 a treatment volume 40 of the individual neck 2a of each container 2 from an external environment 6 containing the body 2d of the container 2. In particular, the treatment volume 40 is comprised between the corresponding filling valve 9 and at least a part of the neck 2a of the container 2. The treatment volume 40 therefore also protects the internal surface of the container 2 which comes into contact with the filling product. The filling apparatus 10 further comprises dispensing means for dispensing a fluid into the treatment volume of each neck 2a so as to flow over the neck 2a of the corresponding container 2 in order to prevent the entry of contaminants into the treatment volume 40.

Preferably, the flow of fluid is of the laminar type.

Figure 1:
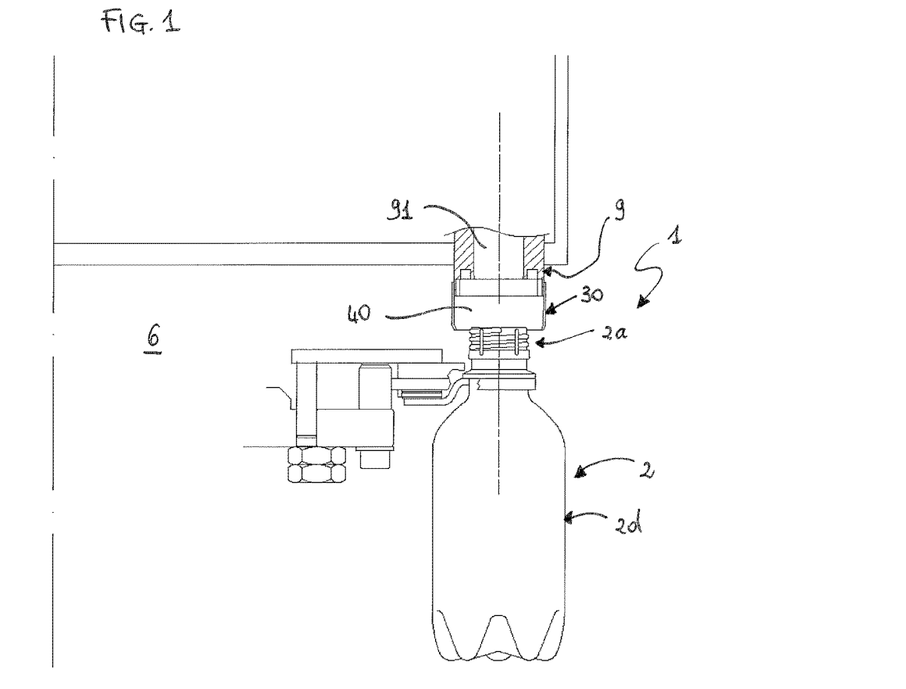
FIG. 1 illustrates a filling station of an apparatus for filing containers with the tubular element in the engagement step of the mouth, according to the present invention, in a sectioned side view.

In the preferred embodiment described and illustrated herein, the means for separating 30 the treatment volume 40 from the external environment 6 comprises, for each filling station 1, a tubular element external and concentric to the corresponding filling valve 9.

In particular, the tubular element 30 can be moved linearly between at least one disengagement configuration and at least one engagement configuration of the mouth 2b of the container 2 placed below the filling valve 9.

In an embodiment not illustrated, the means for separating 30 the treatment volume 40 from the external environment 60 comprises, for each filling station 1, an extendable or reducible bellows in the direction of the mouth 2b of the container 2.

Preferably, the external environment 6 is single and distinct from the individual treatment volumes 40 of each filling station 1. Such treatment volumes 40 are however in fluid communication with the external environment 6.

Figure 1A:
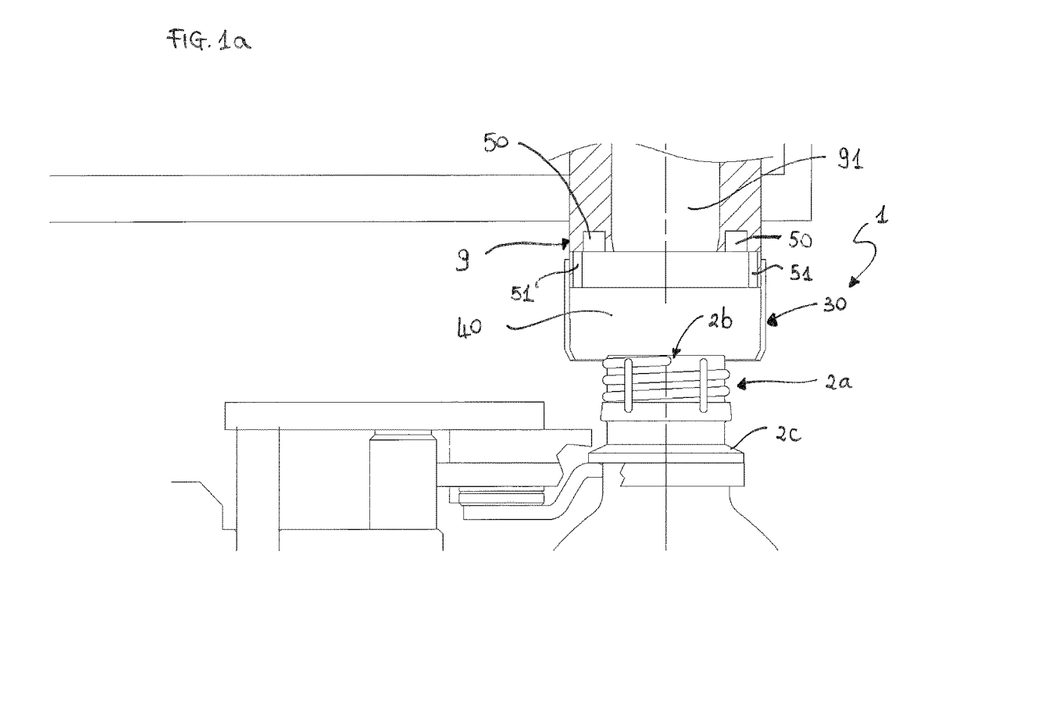
FIG. 1a is an enlargement of a detail of FIG. 1.

Preferably, each treatment volume 40 extends partially around the neck 2a so as to leave the bague 2c of the parison or of the container 2 outside.

In this context, the technical term "bague" means a circumferential protuberance of the neck 2a of the parison or of the container 2, placed below the threaded zone of the neck 2a.

In particular, the filling apparatus 10 has as many tubular elements 30 and as many treatment volumes 40 as the filling stations 1. Each treatment volume 40 is separate and independent from the others. In other words, each container 2 has its treatment volume 40 of the neck 2a separate and not shared with that of the other containers 2.

In the preferred embodiment, the fluid dispensing means comprises a plasma generator (not illustrated) and a plasma transport circuit (not illustrated) from the plasma generator to the treatment volume 40.

Preferably, the transport circuit comprises conduits 50, 51 afforded in the filling valve 9 laterally to a dispensing conduit 91 of the filling product (which is central to the filling valve 9).

Alternatively, the transport circuit comprises an annular conduit to the dispensing conduit 91 of the filling product.

In another embodiment, the transport circuit comprises a plurality of parallel conduits arranged annularly with respect to the dispensing conduit 91 of the filling product.

Preferably, the plasma generator is configured to generate balls of plasma immersed in a gas current. Such technology is known as "plasma balls".

Preferably, the plasma generator consists of the device described in document WO2009/050240.

Such a device allows the plasma to be generated directly in proximity to the neck 2a of the parison or the container 2, exploiting the atmosphere resident therein.

In other words, in each filling station 1 the container 2 is filled and at the same time the atmosphere around the neck 2a of the container 2 is sterilised, therefore the internal surface of the tubular element 30 is also sterilised.

In one embodiment, the fluid dispensing means comprises a source of sterile air. The use of sterile air to maintain the flow in the neck zone 2a is sufficient, for example, for applications in an aseptic packaging line of high-acid products, for which four decimal reductions are generally required.

In a further embodiment, used in aseptic packaging lines of low-acid products, the fluid dispensing means comprises a source of sterilising gas. In a further embodiment, the fluid dispensing means comprises a source of energised water, i.e. a source of Engineered Water Nano Structures, known by the acronym EWNS.

Figure 2:
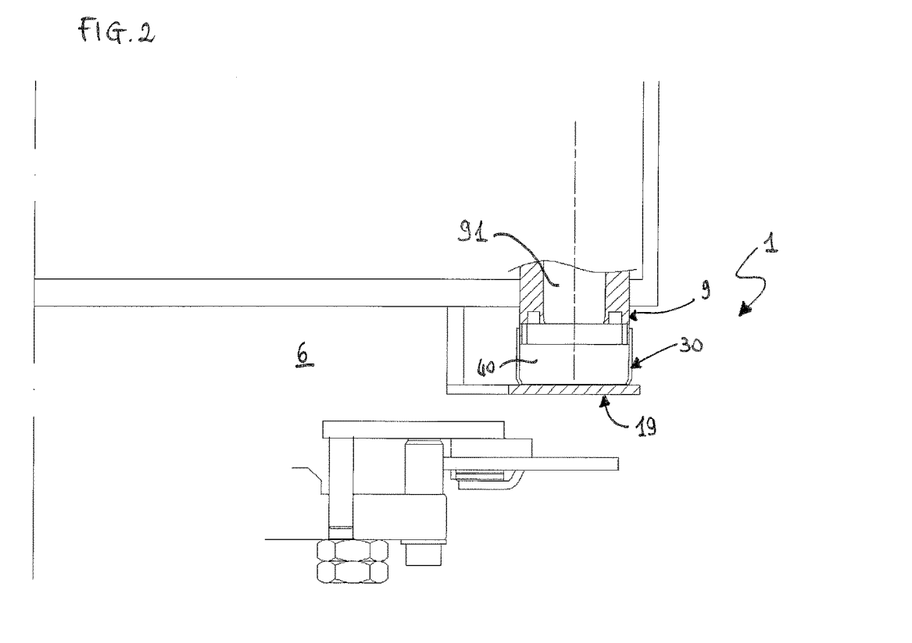
FIG. 2 illustrates the filling station of FIG. 1, during a sanitisation step, according to the present invention, in a sectioned side view.

Preferably, each filling valve 9 is associated with a sanitisation device of the dummy bottle type 19 which can be configured in at least one rest position in which it prevents interference with the filling valve 9 and in one active position in which the dummy bottle 19 is arranged below the filling valve 9 closing the treatment volume 40 so as to prevent fluid communication with the external environment 6.

The use of a dummy bottle sanitisation device is already known (see patent EP0780338 in the name of the Applicant), therefore it will not be described further.

Figure 3:
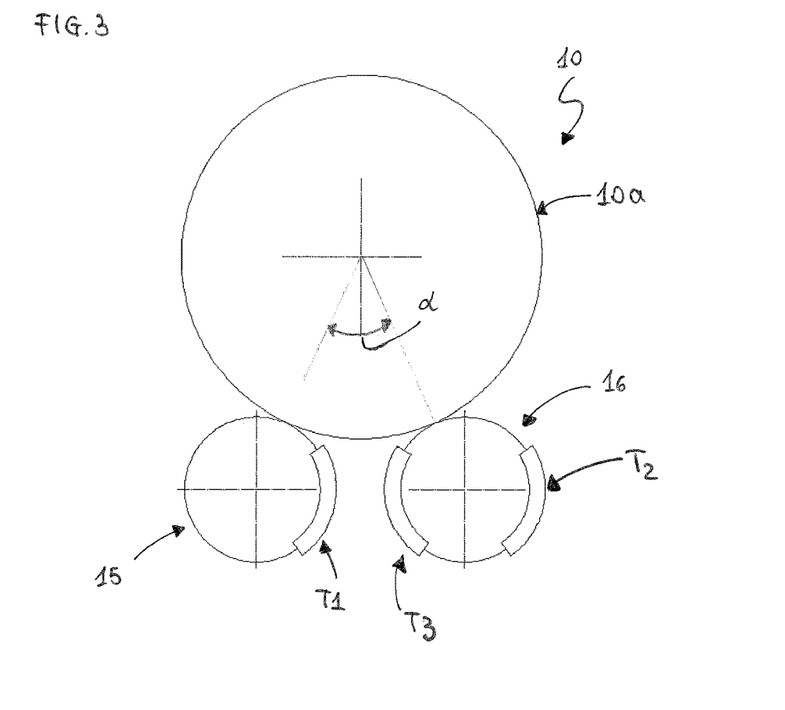
FIG. 3 illustrates an apparatus for filling containers, according to the present invention, in a plan view.

The filling apparatus 10 further comprises:
- a first transfer star 15 positioned upstream of the rotating carousel 10a to transfer to the latter the containers 2 to be filled;
- a second transfer star 16 positioned downstream of the rotating filling carousel 10a to receive the filled containers 2 from the latter.

Figure 6:
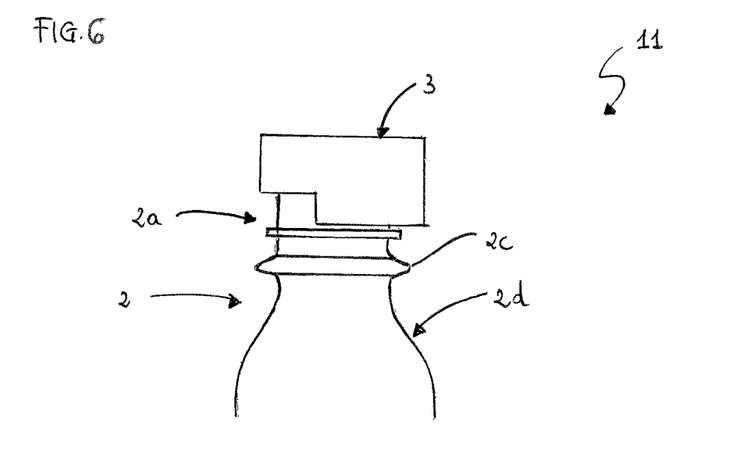
FIGS. 6 and 7 illustrate the neck zone of a container to which a concave shell is applied in a picking station of a transfer star, according to the present invention, in a side view and a sectioned side view, respectively.
Figure 7:
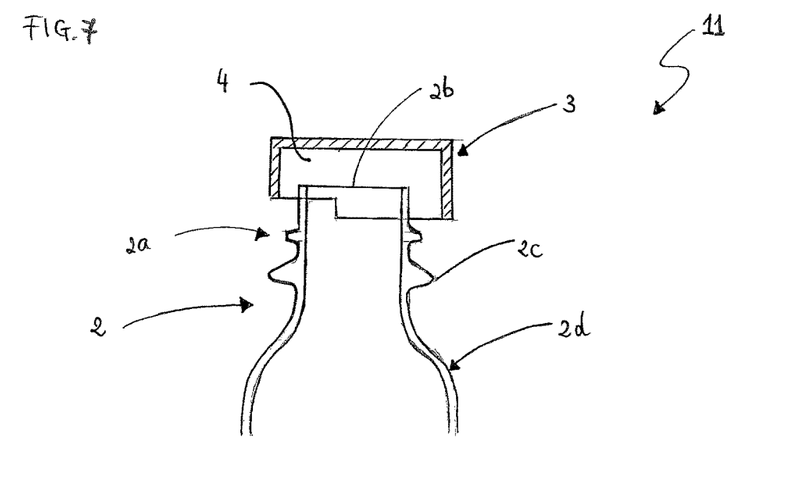

In particular, the first transfer star 15 and the second transfer star 16 have a plurality of picking stations 11 of containers 2, in each of which a concave shell 3 is arranged, configured to be applied to the mouth 2b of the corresponding container 2 so as to be wrapped around the neck 2a at least partially.

Figure 8:
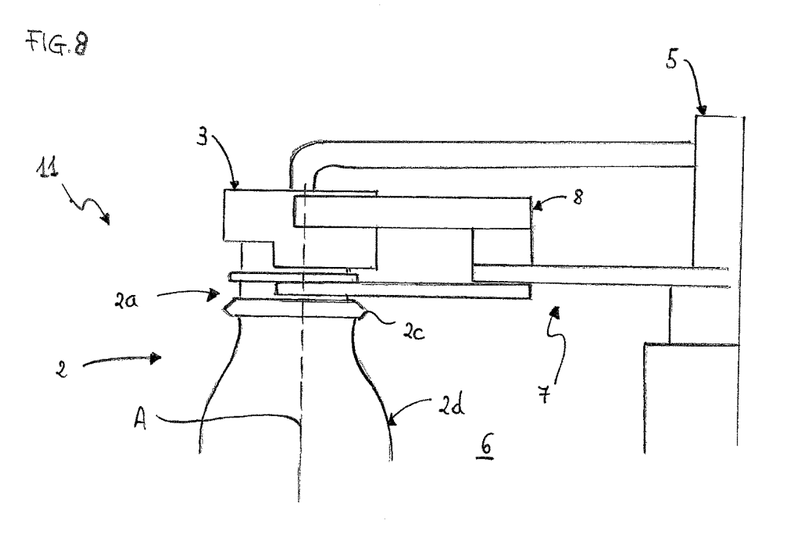
FIG. 8 illustrates a picking station of a container, according to the present invention, in a side view.

In every picking station 11 there are grippers or jaws 20 that grasp the neck 2a of the container 2.

The concave shell 3 therefore delimits a further treatment volume 4 confined around the neck 2a of the individual container 2. For clarity reasons, the treatment volume 40 delimited by the tubular element 30 is called the first treatment volume, while the treatment volume 4 delimited by the concave shell 3 is called the second treatment volume.

Within the second treatment volume 4 a flow of fluid is maintained, which flows over the neck 2a to prevent the entry of contaminants.

Preferably, the flow of fluid within the second treatment volume 4 is of the laminar type.

Preferably, the flow of fluid in the second treatment volume 4 is also obtained here with plasma balls technology. Alternatively, in an aseptic packaging line of high-acid products, the fluid is sterile air.

In an aseptic packaging line of low-acid products, the flow is instead sterilising gas.

In a further embodiment, the fluid is energised water.

Preferably, the second treatment volume 4 extends partially around the neck 2a so as to leave the bague 2c of the parison or of the container 2 outside.

In particular, both the first and the second transfer star 15, 16 have as many concave shells 3 and as many treatment volumes 4 as the picking stations 11. Each second treatment volume 4 is separate and independent from the others. In other words, each container 2 has its second treatment volume 4 of the neck 2a separate and not shared with that of the other containers 2.

Preferably, each concave shell 3 is movable at least between a disengagement configuration and an engagement configuration of the mouth 2b of the parison or the container 2.

For that purpose, a movement means 7 for moving the concave shell 3 is provided.

In the embodiment described and illustrated herein, the movement means 7 for moving the concave shell 3 comprises a guide support 8 on which the concave shell 3 is slidably assembled.

In particular, the guide support 8 has a prevalent extension substantially orthogonal to the axis of symmetry A of the container 2 so that the concave shell 3 can slide orthogonally with respect to the axis of symmetry A.

Figure 9:
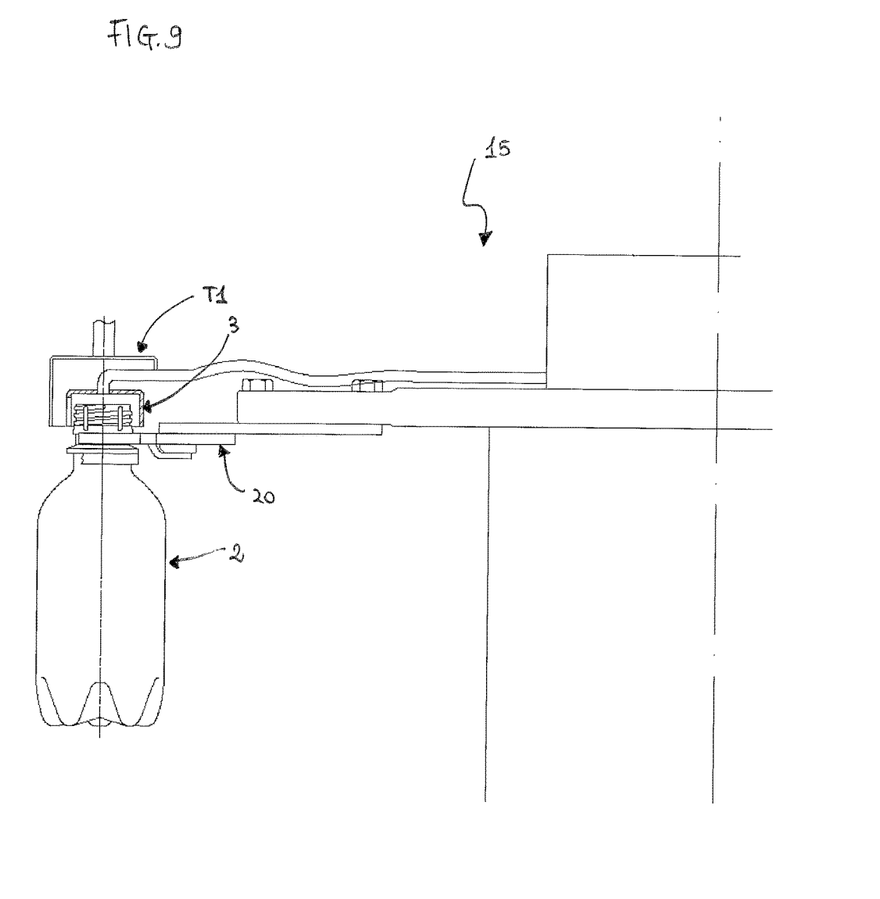
FIG. 9 illustrates part of the first transfer star with the corresponding tunnel, according to the present invention, in a sectioned side view.

Advantageously, the first transfer star 15 comprises:
- a first tunnel T1 having an arched extension that follows the circumferential development of the first transfer star 15 at least for a section that ends in proximity to the rotating carousel 10a;
- first dispensing means for dispensing a cleaning fluid into the first tunnel T1.

In particular, the first tunnel T1 towers over some of the concave shells 3 of the first transfer star 15 so that the cleaning fluid flows over its external surfaces.

Advantageously, the second transfer star 16 comprises:
- a second tunnel T2 having an arched extension that follows the circumferential development of the second transfer star 16 at least for a section that ends in proximity to the rotating filling carousel 10a;
- second dispensing means for dispensing a cleaning fluid into the second tunnel T2.

In particular, the second tunnel T2 towers over some of the concave shells 3 of the second transfer star 16 so that the cleaning fluid flows over its external surfaces.

Preferably, the first and second cleaning fluid dispensing means consists of a plasma generator configured to generate balls of plasma immersed in a gas current.

Alternatively, the first and the second dispensing means dispenses sterile air or ionised air or alcohol.

Figure 10:
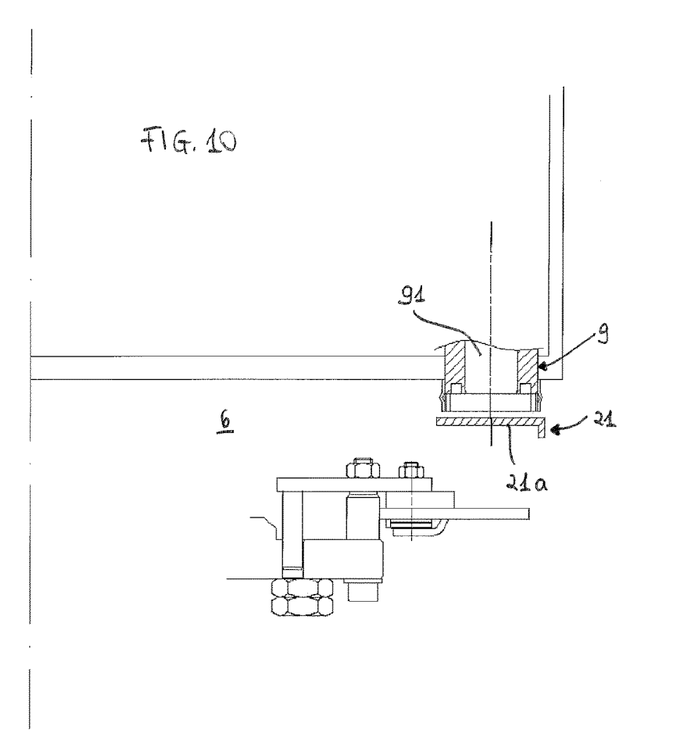
FIG. 10 illustrates the shielding body in the active position below a filling valve, in a sectioned side view.

Preferably, the filling apparatus 10 comprises a shielding body 21 arranged on the filling carousel 10a, which has a circumferential extension along a dead angle α of the filling carousel 10a in which containers 2 do not transit.

In particular, the shielding body 21 can be moved between a rest position wherein it avoids interfering with the dummy bottles 19 (during a sanitisation step) that sweep through the dead angle α and an active position wherein the shielding body 21 is arranged below the filing valves 9 that sweep through the dead angle α to limit inverse air flows from the external environment 6 towards the filling valves 9.

Figure 10A:
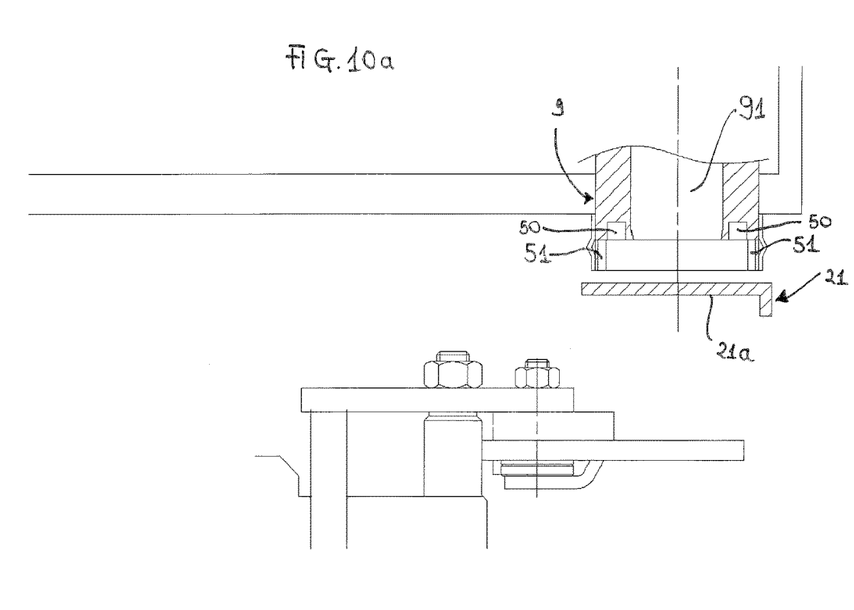
FIG. 10a is an enlargement of a detail of FIG. 10.

In the embodiment described and illustrated herein, the shielding body 21 has an arched plate-like portion 21a which is substantially orthogonal to the rotation axis of the filling carousel 10a.

The method for filling a container, according to the present invention, is described below.

Consider a container 2 placed in a picking station 11 of the first transfer star 15. The container 2 is maintained in a substantially vertical position, with the mouth 2b facing upwards, through corresponding grippers 20, as shown for example in FIG. 8.

The concave shell 3 of the picking station 11 is in the engagement configuration of the mouth 2b of the container 2 so as to be wrapped at least partially around the neck 2a of the container 2 and delimit the second treatment volume 4.

Within the treatment volume 4 a flow of fluid is maintained (e.g. plasma balls) which flows over the neck 2a of the container 2.

Arriving in proximity to the rotating carousel 10a due to the effect of the rotation of the first star 15, the concave shell 3 travels along a stretch below the first tunnel T1 and therefore the cleaning fluid flows over it externally (see FIG. 9).

Figure 4:
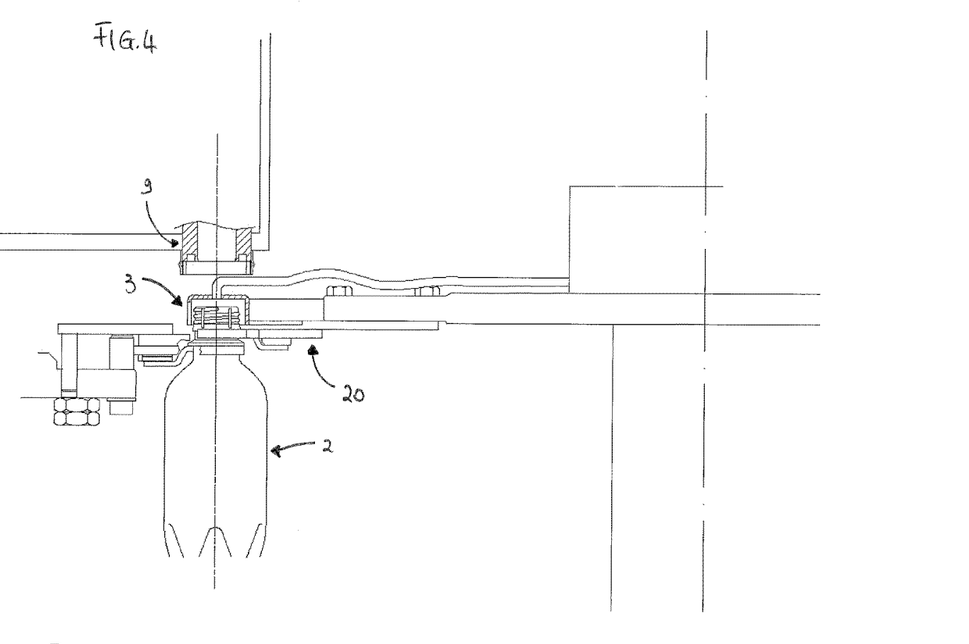
FIGS. 4 and 5 illustrate different moments of the exchange of a container between a transfer star and the rotating carousel, according to the present invention, in a sectioned side view.
Figure 4A:
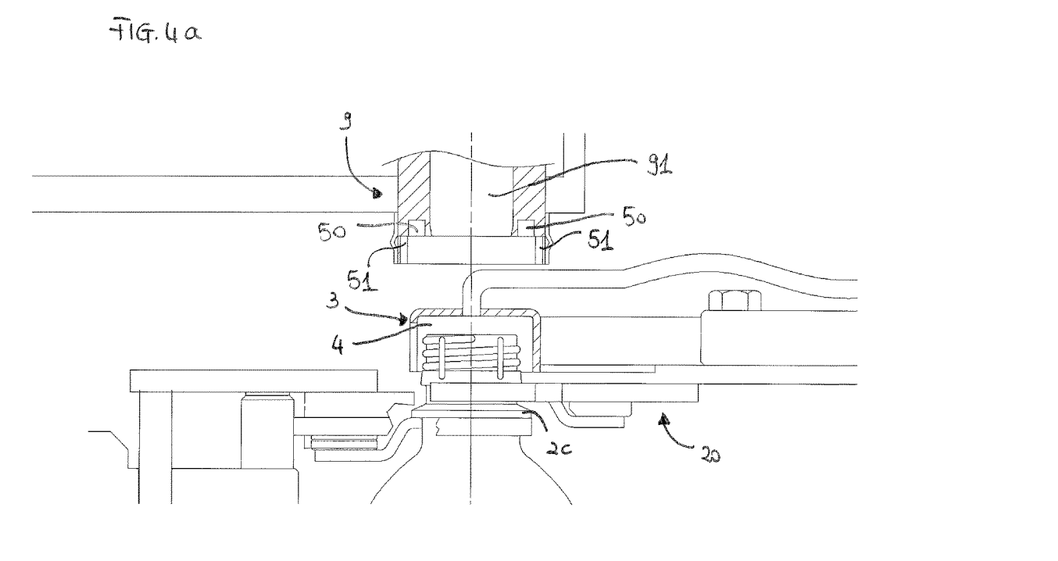
FIG. 4a is an enlargement of a detail of FIG. 4.

When the concave shell 3 is in tangency with the rotating carousel 10a, it can be found below one of the filling valves 9 (see FIGS. 4 and 4a).

Plasma balls or another fluid (e.g. sterile air or sterilising gas) continuously come out from the lateral conduits 50, 51 of the filling valve 9.

The container 2 is released by the grippers 20 of the first star 15 to the rotating carousel 10a (relevant support means is provided).

Figure 5:
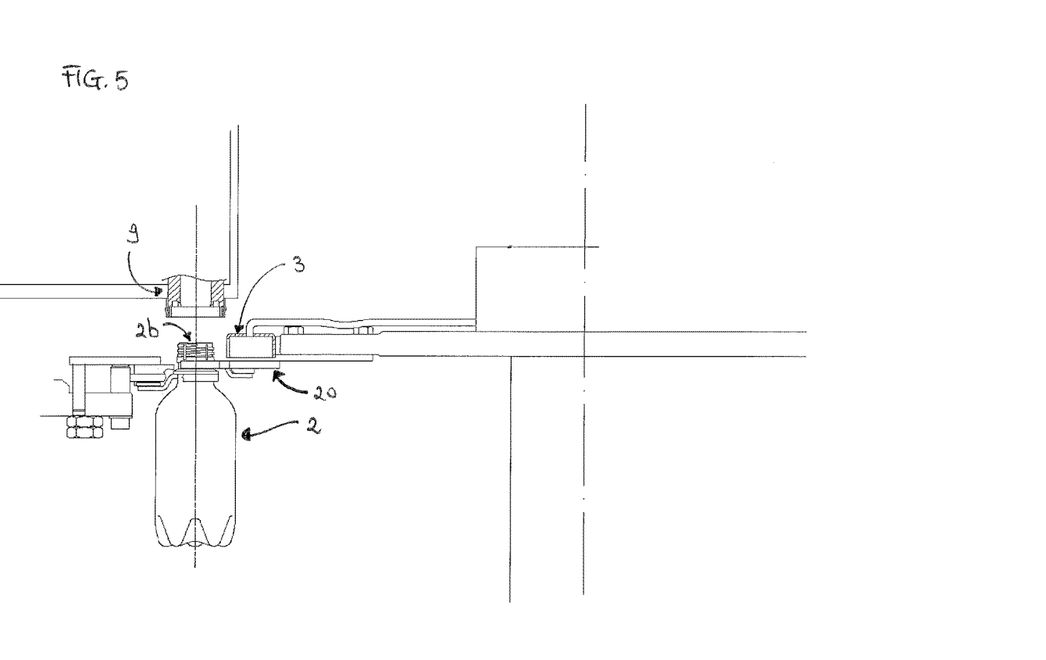
Figure 5A:
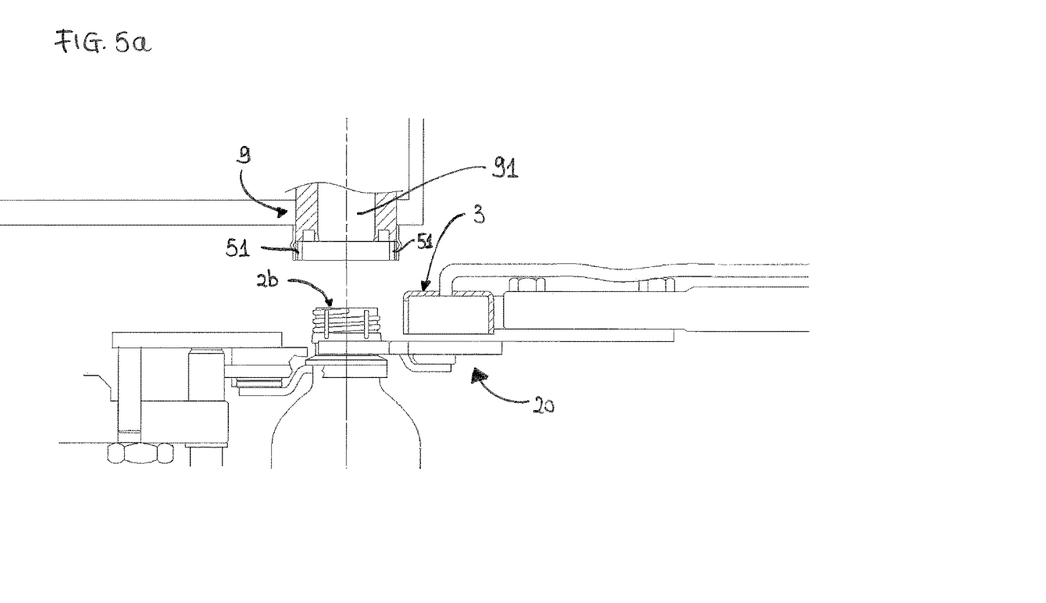
FIG. 5a is an enlargement of a detail of FIG. 5.

By effect of the rotation of the first star 15, the concave shell 3 is moved away. The container 2 always remains below the flow coming from the lateral conduits 50, 51, therefore there is no risk of contamination (see FIGS. 5 and 5a).

The tubular element 30 concentric to the filling valve 9 is therefore fitted onto the mouth 2b so as to assume the engagement configuration of the mouth 2b itself.

Preferably, the tubular element 30 stops above the bague 2c of the container 2.

From the central conduit 91, on the other hand, the filling product is dispensed, for example a drink, which flows into the container 2 below.

Before the outlet of the container 2 from the rotating carousel 10a, the tubular element 30 is raised again, hence assuming the disengagement configuration of the mouth 2b.

At the outlet from the rotating carousel 10a, the container 2 is dropped at a picking station 11 of the second transfer star 15. Such container 2 is therefore protected by the corresponding concave shell 3 which, in the initial rotation stretch of the second star 16, passes below the second tunnel T2.

Figure 12:
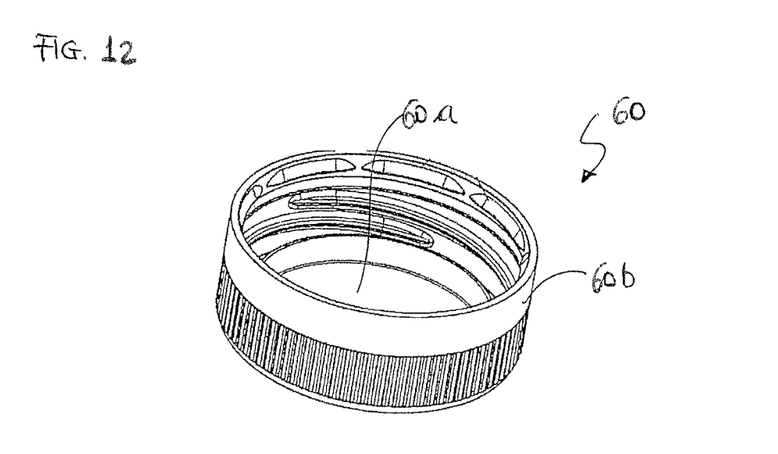
FIG. 12 illustrates a concave closure to be applied to a container, in a perspective view.

Once they have been filled, concave closures or capsules 60 are applied to the containers 2.

In this context, concave closure 60 means a capsule or a cap comprising a base 60a and a lateral surface 60b which extends from the base 60a and defines therewith a cavity (see FIG. 9). On the opposite side to the base 60a, the closure 60 has an opening intended to house the mouth 2b of a container 2.

The application of the concave closure 60 takes place through axial pressure downwards and subsequent screwing around the neck 2a of the container 2. For that purpose, the lateral surface 60b of the closure 60 is internally threaded so as to be able to be screwed to the external thread of the neck 2a of the container 2.

Figure 11:
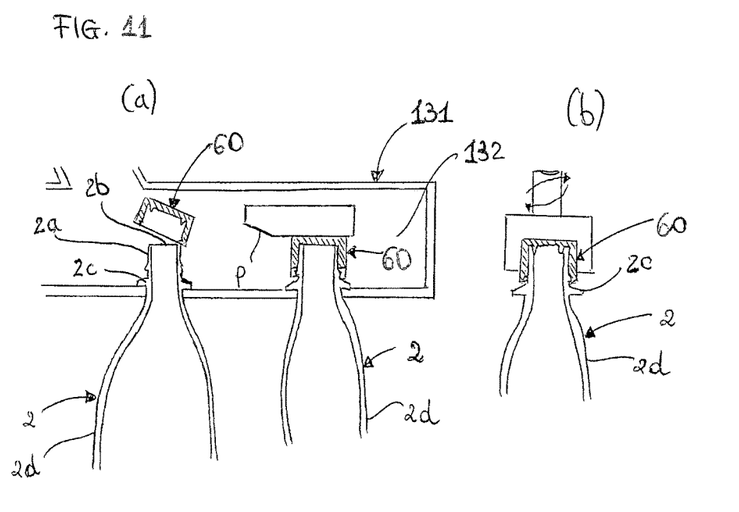
FIGS. 11a and 11b illustrate a rest and pressure step, and a tightening step of a closure on a container.

Preferably, the closure of the container 2 takes place in two distinct steps: an application step of the closure 60 and a tightening step of the closure 60 onto the container 2 itself.

In particular, in the application step, the closure 60 is rested and pressed onto the mouth 2b of the container 2.

In the embodiment described and illustrated herein, the closure 60 is lowered from above onto the mouth 2b of the container 2 using guides. In the bottling sectors, this is known as "a la volée" picking. The pressure of the closure 60 on the mouth 2b takes place by means of an inclined plane P met by the container 2 during its movement.

The concept of "à la volée" picking is already known, for example in non-aseptic cappers, and it will therefore not be described in further detail.

Preferably, the inclined plane P is the lower plane of a circular sector T3 placed above the mouths 2b of the containers 2.

Preferably, the step of applying the closures 60 takes place within a tunnel isolator 131 adapted to define a controlled contamination environment 132 containing at least the neck 2a of the containers 2.

In particular, the controlled contamination environment 132 has a volume that extends into a restricted zone around the neck 2a of the containers 2.

Unlike the concave shells 3 and the tubular elements 30, which individually cover a single neck 2a, here the isolator 131 defines an environment 132 common to all the necks 2a of the containers 2.

In the tightening step, each closure 60 is screwed to the neck 2a of the corresponding container 2 so as to seal it and make the seal definitive.

Preferably, the tightening step is performed in a non-aseptic capper of the known type.

During a sanitisation step of the filling apparatus 1, the dummy bottles 19 assume the active position, therefore they are arranged below the filling valves 9 closing the first treatment volume 40 from below (see FIG. 2). The cleaning is performed using soda or foam substances.

In the sanitisation step, the shielding body 21 at the dead angle α is in the rest position so as not to interfere with the dummy bottles 19.

Vice versa, during filling, the shielding body 21 assumes the active position, therefore it is arranged below the filling valves 9.

The characteristics of the apparatus and method for filling containers, according to the present invention, are clear, as are the advantages.

First of all, the volumes to be sterilised have been further reduced thanks to the fact that in each individual filling station an individual treatment volume of the neck of the container is created.

Hence, the toroidal volume defined by the neck-ring isolator has been replaced by many volumes restricted to the individual neck zones.

The fact that each container has an individual sterile volume, i.e. not shared with that of the other containers, allows quicker and safer maintenance interventions. For example, in the event of hitches, intervention is possible only on the affected container (and therefore on the corresponding treatment volume), while the other treatment volumes are not affected.

Likewise, the format change will be more practical, with a clear reduction in downtime and increased flexibility of the apparatus and the line.

Limiting the treatment volume to the individual neck-zones further allows the sterilisation operations to be concentrated only on the surfaces of the container that effectively need them, i.e. mouth, zone proximal to the neck and inside of the container, avoiding sterilising the external surfaces of the body of containers or extremely extensive volumes (as happens in the toroidal isolator).

The preferred embodiment, using known technology such as plasma balls, allows the flow to be maintained in the neck zone continuously generating the plasma directly in proximity to the neck, exploiting the atmosphere resident therein.

Such technology is particularly suitable for open treatment volumes (such as those defined by the tubular elements and the concave shells) since it is safe technology for the operators and does not require further confinement of the body zones of the containers.

Furthermore, the sterilisation is also substantially concomitant to the transfer step of the container to the filling carousel and to the transfer step of the container from such carousel. Therefore, also the transfer time of the containers becomes useful time as it is used to maintain the sterile conditions in the neck zones.

Therefore it is no longer necessary to have a sterile zone extending to various containers: many restricted and separate sterile zones are sufficient, to place in contact two by two only during the exchange step of the containers between the stars and the filling carousel.

The provision of tunnels in the transfer stars, to cover the concave shells close to the filling carousel further, allows the external surfaces of such shells to be cleaned. In fact, if a dirty shell arrived below a filling valve, the flow of plasma coming from above (which is never interrupted) could flow over the external surfaces of the shell and convey contaminants into the container below or around the mouth.

Furthermore, the use of the shielding body in the dead angle of the filling machine has the function of emulating the neck of the containers so as to reduce the outlet section of the plasma from the lateral conduits of the filling valves. In this way, ambient air is not returned following fluid dynamic turbulence and possible entry of contaminant particles.

What is claimed is:

1. Filling apparatus (10) for filling containers (2) with a filling product, comprising:
   a rotating carousel (10a) having a plurality of filling stations (1) in each of which a filling valve (9) is arranged below which the corresponding container (2) can be positioned with its mouth (2b) facing said filling valve (9);
   means for separating (30) a treatment volume (40) of the individual neck (2a) of each container (2) from an external environment (6) containing the body (2d) of the container (2), said treatment volume (40) being comprised between the corresponding filling valve (9) and at least one part of the neck (2a) of the container (2);
   dispensing means for dispensing a fluid into the treatment volume (40) of each neck (2a) so as to flow over the neck (2a) of the corresponding container (2) in order to prevent the entry of contaminants into said treatment volume (40);
   a first transfer star (15) positioned upstream of said rotating carousel (10a) to transfer to the latter the containers (2) to be filled;
   a second transfer star (16) positioned downstream of said rotating carousel (10a) to receive the filled containers (2) from the latter, said first transfer star (15) and said second transfer star (16) having a plurality of picking stations (11) for the containers (2), characterised in that in each of said picking stations (11) a concave shell (3) is arranged, configured to be applied onto the mouth (2b) of the corresponding container (2) so as to be wrapped at least partially around its neck (2a) in order to delimit a treatment volume (4) of the neck (2a) within which a flow of fluid is maintained that flows over the neck (2a) to prevent the entry of contaminants into said treatment volume (4).

2. Filling apparatus (10) according to claim 1, wherein said means for separating (30) the treatment volume (40) from the external environment (6) comprise, for each filling station (1), a tubular element (30) external and concentric to the corresponding filling valve (9), said tubular element (30) being movable linearly between at least one disengagement configuration and one engagement configuration of the mouth (2b) of the container (2) placed below the filling valve (9).

3. Filling apparatus (10) according to claim 1, wherein said external environment (6) is single and distinct from the individual treatment volumes (40) of the filling stations (1), said treatment volumes (40) being in fluid communication with the external environment (6).

4. Filling apparatus (10) according to claim 1, wherein each filling valve (9) is associated with a sanitisation device of the dummy bottle type (19) which can be configured in at least one rest position in which it prevents interference with the filling valve (9) and in one active position in which said dummy bottle (19) is arranged below the filling valve (9) closing the treatment volume (40) so as to prevent fluid communication with said external environment (6).

5. Filling apparatus (10) according to claim 1, wherein each treatment volume (40) does not contain a bague (2c) of the corresponding container (2).

6. Filling apparatus (10) according to claim 1, wherein said dispensing means comprise:
   a plasma generator;
   a transport circuit for transporting the plasma from said plasma generator to said treatment volume (40), said transport circuit in turn comprising conduits (50, 51) afforded in said filling valve (9) laterally to a dispensing conduit (91) for dispensing the filling product.

7. Filling apparatus (10) according to claim 6, wherein said plasma generator is configured to generate plasma balls immersed in a gas stream.

8. Filling apparatus (10) according to claim 1, wherein said dispensing means comprise a source of sterile air or a source of sterilising gas.

9. Filling apparatus (10) according to claim 1, wherein said first transfer star (15) comprises:
   a first tunnel (T1) having an arched extension that follows the circumferential development of the first transfer star (15) at least for a section that ends in proximity to said rotating carousel (10a);
   first dispensing means of a cleaning fluid into said first tunnel (T1), said first tunnel (T1) towering over some of the concave shells (3) of the first transfer star (15) so that the cleaning fluid flows over their external surfaces.

10. Filling apparatus (10) according to claim 9, wherein said second transfer star (16) comprises:
    a second tunnel (T2) having an arched extension that follows the circumferential development of the second transfer star (16) at least for a section that ends in proximity to said rotating carousel (10a);
    second dispensing means of a cleaning fluid into said second tunnel (T2), said second tunnel (T2) towering over some of the concave shells (3) of the second transfer star (16) so that the cleaning fluid flows over their external surfaces.

11. Filling apparatus (10) according to claim 10, wherein said first and second cleaning fluid dispensing means consist of a plasma generator configured to generate plasma balls immersed in a gas stream.

12. Filling apparatus (10) according to claim 1, further comprising a shielding body (21) arranged on said rotating carousel (10a) which has a circumferential extension along a dead angle (a) of the rotating carousel (10a) in which containers (2) do not transit, said shielding body (21) being moveable between a rest position and an active position in which said shielding body (21) is arranged below the filling valves (9) that sweep through the dead angle (a) to limit inverse air flows from the external environment (6) towards said filling valves (9).

13. Filling apparatus (10) according to claim 12, wherein said shielding body (21) has an arched plate-like portion (21a) which is substantially orthogonal to the rotation axis of said rotating carousel (10a).

* * * * *

UNITED STATES PATENT AND TRADEMARK OFFICE
CERTIFICATE OF CORRECTION

PATENT NO. : 10,287,152 B2
APPLICATION NO. : 15/520366
DATED : May 14, 2019
INVENTOR(S) : Paolo Pagliarini

Page 1 of 1

It is certified that error appears in the above-identified patent and that said Letters Patent is hereby corrected as shown below:

In the Claims

Column 12, Line 45, being Line 2 of Claim 11, delete "cleaning fluid".

Signed and Sealed this
Twenty-seventh Day of August, 2019

Andrei Iancu
*Director of the United States Patent and Trademark Office*